United States Patent [19]
Yokoyama

[11] Patent Number: 4,560,689
[45] Date of Patent: Dec. 24, 1985

[54] HETEROCYCLIC-FUSED PYRAZOLO-[3,4-D]PYRIDIN-3-ONES AS BENZODIAZEPINE RECEPTOR MODULATORS

[75] Inventor: Naokata Yokoyama, Cliffside, N.J.

[73] Assignee: Ciba-Geigy Corporation, Ardsley, N.Y.

[21] Appl. No.: 638,322

[22] Filed: Aug. 6, 1984

Related U.S. Application Data

[62] Division of Ser. No. 457,105, Jan. 10, 1983, Pat. No. 4,479,955.

[51] Int. Cl.$^4$ ............... C07D 471/12; C07D 513/12; C07D 498/12
[52] U.S. Cl. .................... 514/250; 514/254; 514/267; 514/293; 544/234; 544/251; 544/328; 544/345; 546/82; 546/83
[58] Field of Search ............. 546/82, 83; 544/345, 544/234, 251, 328; 514/250, 254, 267, 293

[56] References Cited

U.S. PATENT DOCUMENTS 4,312,870  1/1982  Yokoyama ..................... 546/82
4,479,955  10/1984  Yokoyama ..................... 544/243

FOREIGN PATENT DOCUMENTS 0126970  12/1984  European Pat. Off. ............. 546/82

OTHER PUBLICATIONS

Khan et al., J. Heterocylic Chemistry 20, 475 (1983).
Hoehn, et al., CA 81: 105500p.
Hoehn et al., CA 77: 5457d.
Khan et al., The Synthesis of Thieno (3,2-e) Pyrazolo[4,3-c]Pyridine Heterocyle, vol. 6, No. 6, 1977, pp. 727–729.
Pyrazolo (3,4-d) Thieno (2,3-b) Pyridines.

Primary Examiner—Henry R. Jiles
Assistant Examiner—P. Ann Bucci
Attorney, Agent, or Firm—Norbert Gruenfeld

[57] ABSTRACT

Disclosed are heterocyclic-fused pyrazolo[3,4-d]pyridin-3-ones useful as benzodiazepine receptor modulators.

11 Claims, No Drawings

HETEROCYCLIC-FUSED PYRAZOLO-[3,4-D]PYRIDIN-3-ONES AS BENZODIAZEPINE RECEPTOR MODULATORS

REFERENCE TO RELATED APPLICATIONS

This is a division of application Ser. No. 457,105 filed Jan. 10, 1983, now U.S. Pat. No. 4,479,955.

SUMMARY OF THE INVENTION

The present invention is directed to 2-substituted [b]-heterocycle-fused pyrazolo-[3,4-d]pyridin-3-ones of the formula IA or IB which are benzodiazepine receptor ligands and modulators demonstrating useful nervous system regulatory activity, e.g. psychoactive, such as anxiolytic, and anticonvulsant activity.

The foregoing attributes render compounds of this invention particularly useful when administered, alone or in combination, to mammals for the treatment of e.g. nervous system disorders, such as anxiety, and convulsive conditions (epilepsy). Compounds of the invention may also be useful as antidepressants, as somnolytics, as appetite suppressants, as antagonists (antidotes) of the effects of benzodiazepine drugs on the central nervous system, as well as antagonists of the sedative effects of alcohol and benzodiazepine drugs in combination.

DETAILED DISCLOSURE OF THE INVENTION

This invention relates to novel 2-substituted-[b]-heterocycloe-fused pyrazolo[3,4]-pyridin-3-ones, useful as e.g. benzodiazepine receptor modulators, processes for preparing the same, pharmaceutical compositions comprising said compounds and methods of treating e.g. nervous system disorders by administration of said compounds and compositions to mammals.

Particularly the invention relates to compounds of formula IA or IB

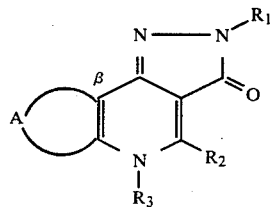

(IA)

or

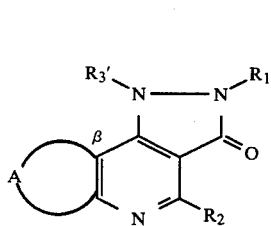

(IB)

wherein A represents a 3-membered bivalent residue completing a fused five-membered unsaturated heterocyclic ring containing one sulfur, oxygen, or unsubstituted or lower alkyl substituted amino nitrogen atom, and wherein the carbon atoms in said residue are unsubstituted or one of them is substituted by lower alkyl, carbo-(lower)-alkoxy, halogen or trifluoromethyl; or A represents a 3-membered bivalent residue completing a fused five-membered unsaturated heterocyclic ring containing two nitrogen atoms separated by a carbon atom, one of which is unsubstituted or lower alkyl substituted amino nitrogen and the other is imino nitrogen, and wherein the carbon atom is unsubstituted or substituted by lower alkyl, phenyl, or phenyl monosubstituted by lower alkyl, lower alkoxy, halogen or trifluoromethyl; or A represents a 3-membered bivalent residue completing a fused five-membered unsaturated heterocyclic ring containing one nitrogen atom and one oxygen or sulfur atom, and wherein the carbon atom in said residue is unsubstituted or substituted by lower alkyl, lower alkoxy, halogen or trifluoromethyl; or A represents a 4-membered bivalent residue completing a fused six-membered unsaturated heterocyclic ring containing one nitrogen atom, wherein the nitrogen atom is not directly attached to the $\beta$-carbon of the ring system, and wherein the carbon atoms in said residue are unsubstituted or substituted by one to three radicals selected from lower alkyl, lower alkoxy, halogen and trifluoromethyl; or A represents a 4-membered bivalent residue completing a fused six-membered unsaturated heterocyclic ring containing two nitrogen atoms, and the carbon atoms in said residue are unsubstituted or substituted by one or two radicals selected from lower alkyl, lower alkoxy, halogen and trifluoromethyl;

$R_1$ represents phenyl or phenyl substituted by one or two radicals selected from lower alkyl, lower alkoxy, halogen and trifluoromethyl; or $R_1$ represents a five-membered unsaturated heterocyclic radical containing one hetero atom selected from sulfur, oxygen and unsubstituted or lower alkyl substituted amino nitrogen, or a said radical containing two hetero atoms consisting of one imino nitrogen and one member selected from unsubstituted or lower alkyl substituted amino nitrogen, sulfur and oxygen; or $R_1$ represents an unsaturated six membered heterocyclic radical containing one or two nitrogen atoms; or $R_1$ represents a bicyclic benzo-fused five membered unsaturated heterocyclic radical containing one hetero atom selected from sulfur, oxygen and unsubstituted or lower alkyl substituted amino nitrogen; or $R_1$ represents a bicyclic benzo-fused five membered unsaturated heterocyclic radical containing two hetero atoms consisting of one imino nitrogen and one member selected from unsubstituted or lower alkyl substituted amino nitrogen, oxygen and sulfur; or $R_1$ represents a bicyclic benzo-fused six membered unsaturated heterocyclic radical containing one or two nitrogen atoms; or $R_1$ represents any of said heterocyclic radicals mono- or di-substituted on carbon by lower alkoxy, lower alkyl or halogen;

$R_2$, $R_3$ and $R_3'$ independently represent hydrogen or lower alkyl; or tautomers thereof; or salts thereof, particularly pharmaceutically acceptable salts.

Preferred are the compounds of formula IA or IB wherein A together with the two carbon atoms to which it is attached represents a fused unsaturated heterocyclic ring selected from (a) thieno, furo, and N-unsubstituted or N-lower alkyl substituted pyrrolo, wherein the carbon atoms in any of said rings are unsubstituted or one of them is substituted by lower alkyl, carbo-(lower)-alkoxy, halogen or trifluoromethyl; (b) N-unsubstituted or N-lower alkyl substituted-imidazo, wherein the carbon atom in said ring is unsubstituted or substituted by lower alkyl, lower alkoxy, halogen or trifluoromethyl; (c) thiazolo, oxazolo, isoxazolo, 2,3-, 3,4- or 4,3-pyrido, and pyridazino, wherein the carbon atoms forming any of said rings are unsubstituted or one or two are substituted by lower alkyl, lower alkoxy or halogen; (d) pyrimido and pyrazino wherein the carbon atoms in any of said rings are unsubstituted or one is substituted by lower alkyl or lower alkoxy; $R_1$ represents phenyl, or phenyl mono- or disubstituted by lower alkyl, lower alkoxy, halogen or trifluoromethyl; or $R_1$ represents an aromatic heterocyclic radical selected from pyridyl, quinolyl, isoquinolyl, pyrimidyl and thiazolyl, or any said heterocyclic radical mono- or di-substituted by lower alkyl, lower alkoxy or halogen; and $R_2$, $R_3$ and $R_3'$ independently represent hydrogen or lower alkyl; or pharmaceutically acceptable salts thereof.

The said above-cited compounds of formula IA or IB represent the $R_1$-substituted-(thieno, furo, pyrrolo, imidazo, thiazolo, oxazolo, isoxazolo, pyrido, pyridazino, pyrimido or pyrazino)-pyrazolo[2,3-d]pyridin-3-ones as defined above.

Particularly preferred are said compounds of formula IA or IB wherein A is as above; $R_2$, $R_3$ and $R_3'$ are hydrogen; and (a) wherein $R_1$ is phenyl or phenyl mono-substituted by lower alkyl, lower alkoxy or halogen;

(b) wherein $R_1$ is 2-pyridyl, 5-(methyl, methoxy or chloro)-2-pyridyl, 3-pyridyl, 6-(methyl or methoxy)-3-pyridyl or 4-pyridyl;

(c) wherein $R_1$ is 3-pyrimidyl, 5-(methyl, methoxy or chloro)-2-pyrimidyl, 4-pyrimidyl or 5-pyrimidyl;

(d) wherein $R_1$ is thiazolyl or 5-(methyl, methoxy or chloro)-2-thiazolyl;

(e) wherein $R_1$ is 2-quinolyl, 3-quinolyl, or 7-chloro-4-quinolyl; and (f) wherein $R_1$ is 1-isoquinolyl; tautomers thereof; or pharmaceutically acceptable salts thereof.

One particular embodiment of the invention is directed to pyrido-pyrazolo[3,4-d]pyridin-3-ones (namely pyrazolo[4,3-c]-[1,6], [1,7] or [1,8]-naphthyridin-3-ones) and is represented by compounds of formula IA or IB wherein A together with the two carbon atoms to which it is attached represents fused 2,3-, 3,4- or 4,3-pyrido (preferably 3,4- or 4,3-pyrido), or any of said pyrido rings mono- or di-substituted by lower alkyl, lower alkoxy or halogen; $R_1$, $R_2$, $R_3$ and $R_3'$ have meaning as given above; or pharmaceutically acceptable salts thereof.

Another embodiment of the invention is directed to thieno-pyrazolo[3,4-d]pyridin-3-ones, and is represented by compounds of formula IA or IB wherein A together with the two carbon atoms to which it is attached represents fused 2,3- or 3,2-thieno, and the carbon atoms in said thieno ring are unsubstituted or one is substituted by lower alkyl, carbo-(lower)-alkoxy, halogen or trifluoromethyl; $R_1$, $R_2$, $R_3$ $R_3'$ have meaning as given above; or pharmaceutically acceptable salts thereof.

Another embodiment of the invention is directed to imidazo-pyrazolo[3,4-d]pyridin-3-ones, and is represented by compounds of formula IA or IB wherein A together with the two carbon atoms to which it is attached represents fused N-unsubstituted or N-lower alkyl substituted 5,4-imidazo, and the carbon atoms in said 5,4-imidazo ring is unsubstituted or substituted by lower alkyl, phenyl or phenyl mono-substituted by lower alkyl, lower alkoxy, halogen, or trifluoromethyl; $R_1$, $R_2$, $R_3$ and $R_3'$ have meanings as given above; or pharmaceutically acceptable salts thereof.

Further preferred are the said pyrazolo[4,3-c][1,6]naphthyridin-3(5H)-ones of formula II

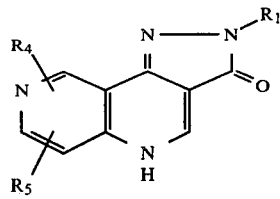

(II)

wherein $R_1$ represents phenyl or phenyl mono- or disubstituted by lower alkyl, lower alkoxy, halogen or trifluoromethyl; or $R_1$ represents an aromatic heterocyclic radical selected from pyridyl, quinolyl, isoquinolyl, pyrimidyl and thiazolyl, or any said radical mono- or disubstituted by lower alkyl, lower alkoxy or halogen; $R_4$ and $R_5$ represent independently hydrogen, lower alkyl, lower alkoxy or halogen; or tautomers thereof; or pharmaceutically acceptable salts thereof.

Particularly preferred are compounds of formula II (a) wherein $R_1$ is phenyl or phenyl mono-substituted by lower alkyl, lower alkoxy or halogen; $R_4$ is halogen, methoxy, methyl, fluoro or chloro; $R_5$ is hydrogen; or tautomers thereof; or pharmaceutically acceptable salts thereof.

(b) wherein $R_1$ is 2-pyridyl, 5-(methyl, methoxy or chloro)-2-pyridyl, 3-pyridyl, 6-(methyl or methoxy)-3-pyridyl or 4-pyridyl; $R_4$ is hydrogen, methyl, methoxy, fluoro or chloro; $R_5$ is hydrogen; or tautomers thereof; or pharmaceutically acceptable salts thereof.

(c) wherein $R_1$ is 2-pyrimidyl, 5-(methyl, methoxy or chloro)-2-pyrimidyl, 4-pyrimidyl or 5-pyrimidyl; $R_4$ is hydrogen, methoxy, methyl, fluoro or chloro; $R_5$ is hydrogen; or tautomers thereof; or pharmaceutically acceptable salts thereof.

(d) wherein $R_1$ is 2-thiazolyl or 5-(methyl, methoxy or chloro)-2-thiazolyl; $R_4$ is hydrogen, methoxy, methyl, fluoro or chloro; $R_5$ is hydrogen; or tautomers thereof; or pharmaceutically acceptable salts thereof.

(e) wherein $R_1$ is 2-quinolyl, 3-quinolyl, or 7-chloro-4-quinolyl; $R_4$ is hydrogen, methyl, fluoro or chloro; $R_5$ is hydrogen; or tautomers thereof; or pharmaceutically acceptable salts thereof; and (f) wherein $R_1$ is 1-isoquinolyl; $R_4$ is hydrogen, methoxy, methyl, fluoro or chloro; $R_5$ is hydrogen; or tautomers thereof; or pharmaceutically acceptable salts thereof.

Also preferred are the pyrazolo[4,3-c][1,7]-naphthridin-3-ones of formula III

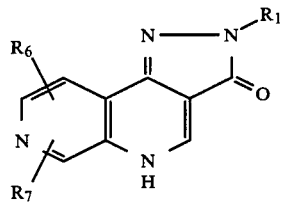

(III)

wherein $R_1$ represents phenyl or phenyl mono- or disubstituted by lower alkyl, lower alkoxy, halogen or trifluoromethyl; or $R_1$ represents an aromatic heterocyclic radical selected from pyridyl, quinolyl, isoquinolyl, pyrimidyl and thiazolyl, or any said radical mono- or disubstituted by lower alkyl, lower alkoxy or halogen; $R_6$ and $R_7$ represent independently hydrogen, lower alkyl, lower alkoxy or halogen; or tautomers thereof; or pharmaceutically acceptable salts thereof.

Particularly preferred are compounds of formula III (a) wherein $R_1$ is phenyl or phenyl mono-substituted by lower alkyl, lower alkoxy or halogen; $R_6$ is hydrogen, methoxy, methyl, fluoro or chloro; $R_7$ is hydrogen; or tautomers thereof; or pharmaceutically acceptable salts thereof.

(b) wherein $R_1$ is 2-pyridyl, 5-(methyl, methoxy or chloro)-2-pyridyl, 3-pyridyl, 6-(methyl or methoxy)-3-pyridyl or 4-pyridyl; $R_6$ is hydrogen, methyl, methoxy, fluoro or chloro; $R_7$ is hydrogen; or tautomers thereof; or pharmaceutically acceptable salts thereof.

(c) wherein $R_1$ is 2-pyrimidyl, 5-(methyl, methoxy or chloro)-2-pyrimidyl, 4-pyrimidyl or 5-pyrimidyl; $R_6$ is hydrogen, methoxy, methyl, fluoro or chloro; $R_7$ is hydrogen, or tautomers thereof; or pharmaceutically acceptable salts thereof; and (d) wherein $R_1$ is 2-thiazolyl or 5-(methyl, methoxy or chloro)-2-thiazolyl; $R_6$ is hydrogen, methoxy, methyl, fluoro or chloro; $R_7$ is hydrogen; or tautomers thereof; or pharmaceutically acceptable salts thereof.

Also preferred are the thieno[2,3-b]pyrazolo[3,4-d]-pyridin-3-ones of formula IV

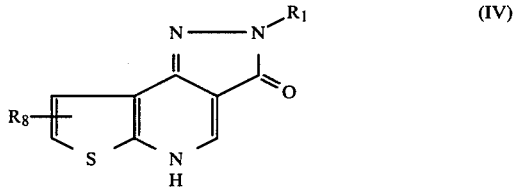

wherein $R_1$ represents phenyl or phenyl mono- or di-substituted by lower alkyl, lower alkoxy, halogen or trifluoromethyl; or an aromatic heterocyclic radical selected from pyridyl, quinolyl, isoquinolyl, pyrimidyl and thiazolyl, or any said heterocyclic radical mono- or disubstituted by lower alkyl, lower alkoxy or halogen; $R_8$ represents hydrogen, lower alkyl, carbo-(lower)alkoxy, halogen or trifluoromethyl; or tautomers thereof; or pharmaceutically acceptable salts thereof.

Particularly preferred are compounds of formula IV (a) wherein $R_1$ is phenyl or phenyl mono-substituted by lower alkyl, lower alkoxy or halogen; or tautomers thereof; or pharmaceutically acceptable salts thereof.

(b) wherein $R_1$ is 2-pyridyl, 5-(methyl, methoxy or chloro)-2-pyridyl, 3-pyridyl, 6-(methyl or methoxy)-3-pyridyl or 4-pyridyl; $R_8$ is hydrogen or halogen; or tautomers thereof; or pharmaceutically acceptable salts thereof; and (c) wherein $R_1$ is 2-thiazolyl or 5-(methyl, methoxy or chloro)-2-thiazolyl; $R_8$ is hydrogen or halogen; or tautomers thereof; or pharmaceutically acceptable salts thereof.

Also preferred are thieno[3,2-b]pyrazolo[3,4-d]pyridin-3-ones of formula V

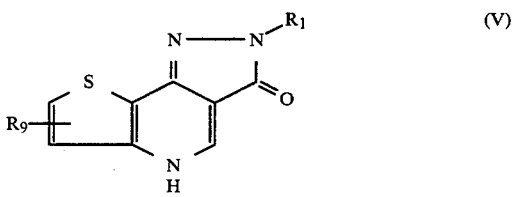

wherein $R_1$ represents phenyl or phenyl mono- or disubstituted by lower alkyl, lower alkoxy, halogen or trifluoromethyl; or an aromatic heterocyclic radical selected from pyridyl, quinolyl, isoquinolyl, pyrimidyl and thiazolyl, or any said heterocyclic radical mono- or disubstituted by lower alkyl, lower alkoxy or halogen; $R_9$ represents hydrogen, lower alkyl, carbo-(lower)-alkoxy, halogen or trifluormethyl; or tautomers thereof; or pharmaceutically acceptable salts thereof.

Particularly preferred are compounds of formula V (a) wherein $R_1$ is phenyl or phenyl mono-substituted by lower alkyl, lower alkoxy or halogen; $R_9$ is hydrogen or halogen; or tautomers thereof; or pharmaceutically acceptable salts thereof; and (b) wherein $R_1$ is 2-pyridyl, 5-(methyl, methoxy or chloro)-2-pyridyl, 3-pyridyl, 6-(methyl or methoxy)-3-pyridyl or 4-pyridyl; $R_9$ is hydrogen or halogen; or tautomers thereof; or pharmaceutically acceptable salts thereof.

Also preferred are the imidazo[b 4,5-b]pyrazolo[3,4-d]pyridin-3-ones of formula VI

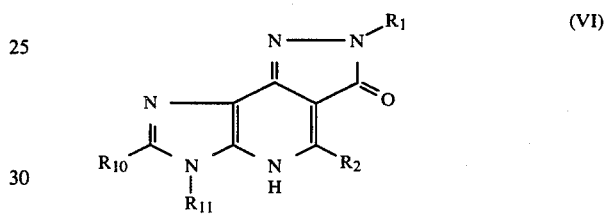

wherein $R_1$ represents phenyl or phenyl mono- or disubstituted by lower alkyl, lower alkoxy, halogen or trifluoromethyl; or an aromatic heterocyclic radical selected from pyridyl, quinolyl, isoquinolyl, pyrimidyl and thiazolyl, or any said heterocyclic radial substituted by lower alkyl, lower alkoxy or halogen; $R_2$ represents hydrogen or lower alkyl; $R_{10}$ represents hydrogen, lower alkyl, phenyl or phenyl monosubstituted by lower alkyl, lower alkoxy, halogen or trifluoromethyl; $R_{11}$ represents hydrogen or lower alkyl; or tautomers thereof; or pharmaceutically acceptable salts thereof.

Particularly preferred are compounds of formula VI (a) wherein $R_1$ is phenyl or phenyl mono-substituted by lower alkyl, lower alkoxy or halogen; $R_2$, $R_{10}$ and $R_{11}$ are independently hydrogen or methyl; or tautomers thereof; or pharmaceutically acceptable salts thereof; and (b) wherein $R_1$ is 2-pyridyl, 5-(methyl, methoxy or chloro)-2-pyridyl, 3-pyridyl, 6-(methyl or methoxy)-3-pyridyl or 4-pyridyl; $R_2$, $R_{10}$ and $R_{11}$ are independently hydrogen or methyl; or tautomers thereof; or pharmaceutically acceptabls salts thereof.

The general definitions used herein have the following meaning within the scope of the present invention.

The term "lower" referred to above and hereinafter in connection with organic radicals or compounds respectively defines such with up to and including 7, preferably up and including 4 and advantageously one or two carbon atoms.

Halogen is preferably fluoro or chloro, but may also be bromo or iodo.

A lower alkyl group or such present in said lower alkoxy, or other alkylated groups, is above all methyl, but also ethyl, n- or i-(propyl, butyl, pentyl, hexyl or heptyl), e.g. 2-methylpropyl or 3-methylbutyl. Carbo(- lower)alkoxy represents lower alkoxy-carbonyl, e.g. ethoxy- or methoxycarbonyl.

Pyridyl represents 2-,3- or 4-pyridyl, advantageously 3-pyridyl.

Quinolyl represents preferably 2-, 3- or 4-quinolyl, advantageously 3-quinolyl.

Isoquinolyl represents preferably 1-, 3- or 4-isoquinolyl, advantageously 1-, 3- or 4-isoquinolyl, advantageously 1-isoquinolyl.

Pyrimidyl represents 2-, 4- or 5-pyrimidyl, preferably 2- or 5-pyrimidyl.

Thiazolyl represents preferably 2-thiazolyl.

The compounds of the invention wherein $R_3$ and $R_3'$ are hydrogen may be represented by either of the tautomeric structure IA or IB, preferably structure IA; furthermore said 3-oxo compounds may, under certain conditions, also exist as the 3-hydroxy tautomers; all of these tautomers are within the scope of the present invention. Said compounds form, especially in the form of the 3-hydroxy compounds, salts with strong bases, and the salts are preferably alkali metal, e.g. sodium or potassium salts of the 1- or 5-unsubstituted compounds ($R_3$ and $R_3'$=H).

Furthermore the compounds of Formula IA or IB, form acid addition salts, which are preferably such of pharmaceutically acceptable inorganic or organic acids, such as strong mineral acids, for example hydrohalic, e.g. hydrochloric or hydrobromic acid; sulfuric, phosphoric or nitric acid; aliphatic or aromatic carboxylic or sulfonic acids, e.g. acetic, propionic, succinic, glycolic, lactic, malic, tartaric, gluconic, citric, maleic, fumaric, hydroxymaleic, pyruvic, phenylacetic, benzoic, 4-aminobenzoic, anthranilic, 4-hydroxybenzoic, salicylic, 4-aminosalicylic, pamoic, nicotinic; methanesulfonic, ethanesulfonic, hydroxyethanesulfonic, benzenesulfonic, p-toluenesulfonic, naphthalenesulfonic, sulfanilic, cyclohexylsulfamic acid; or ascorbic acid.

The compounds of the invention exhibit valuable pharmacological properties, e.g. nervous system regulatory effects, by inter alia modulating the benzodiazepine receptor activity in mammals. The compounds are thus useful for the treatment of nervous system diseases, e.g. those responsive to benzodiazepine receptor modulation.

The compounds of the invention bind to the benzodiazepine receptor and exhibit e.g. anxiolytic and/or anticonvulsant effects, or antagonism of the effects of benzodiazepine drugs. Said effects are demostrable by in vitro and in vivo tests, using advantageously mammals, e.g. mice, rats, or monkeys, as test objects. Said compounds can be applied to them enterally or parenterally, advantageously orally, or subcutaneously, intravenously or intraperitoneally, for example, within gelatin capsules or in the form of starchy suspensions or aqueous solutions or suspensions respectively. The applied dosage may range between 0.1 and 100 mg/kg/day, preferably between about 0.1 and 50 mg/kg/day, advantageously between about 1 and 30 mg/kg/day.

The benzodiazepine receptor binding properties indicative of the nervous system regulatory activity of said new compounds are determined in the receptor binding assay in vitro, e.g. as described in Nature 266, 732 (1977) or Proc. Nat. Acad. Sci. USA 74, 3805 (1977). Diazepam binds specifically and with high affinity to crude synaptosomal membrane preparations from rat fore-brain. This binding is inhibited by other anxiolytic compounds. When tritiated diazepem is used, the interaction of other drugs with said receptor can be readily assessed thus: membranes from rat fore-brain are incubated at 0°–5° for 30 minutes with 2 nM tritiated diazepam and various concentrations of the test substance in a buffer medium maintained at pH 7.5. Solutions of the various concentrations of test substances are prepared by dilution of a 4.2 mM stock solution in dimethylacetamide-ethanol (1:10) with 50 mM pH7.5. Tris-HCl buffer. The membranes, containing the receptors with various amounts of tritiated diazepam, are filtered onto glass fiber filters, which are then analyzed in a liquid scintillation counter. The concentration of the compounds of this invention, required to inhibit the specific binding of 2 nM of tritiated diazepam by 50%, i.e. the $IC_{50}$, is determined graphically.

In vivo benzodiazepine receptor binding is determined essentially as described in Eur. J. Pharmacol. 48, 213 (1978) and Nature 275, 551 (1978).

Test compounds in a corn starch vehicle are administered orally or intraperitoneally to mice or rats. Thirty minutes later, 3H-flunitrazepam (2 nmoles/Kg in saline) is injected into the tail vein, and the animals are sacrificed 20 minutes after injection of the flunitrazepam. The brains are then assayed by determining radioactivity in a liquid scintillation counter for binding of the radioligand to the receptors. A decrease in the binding of 3H-flunitrazepam in the drug-treated animals (as compared with the binding observed in animals treated with vehicle alone) is indicative of benzodiazepine receptor binding by the test compound.

Anxiolytic effects are observed, for example, according to the Cook-Davidson conflict procedure, using male Wistar rats which are maintained at 80% of normal body weight by dietary-, but not water-restriction. They are trained to press a lever within a conditioning chamber, also containing a liquid dipper, a house light, a speaker and a grid-floor. Both lever and grid are connected to an electrical shock source and the chamber is situated in a sound-attenuated room in which a white noise-source is activated during testing, in order to mask any extraneous auditory cues. Each session of 47 minutes duration consists of two alternating schedules. The first is a Variable Interval (VI) schedule of 30 seconds, lasting for 5 minutes, during which a sweetened, condensed milk reinforcement is delivered following the first lever-press after an average of 30 seconds have elapsed, and a drug-induced decrement of this performance is taken as an indication of a neurological deficit. Immediately following the VI-schedule both a 1000 Hz tone and a light-cue are activated, indicating the commencement of the second Fixed Ratio (FR) schedule, lasting for 2 minutes, wherein the milk reinforcement is delivered concomitant with an electric foot shock immediately following the tenth response, thereby establishing a conflict situation. The intensity of said shock ranges between 2.0 and 3.6 mA, varying with each animal, in order to adjust them to about 25–100 responses during this schedule over the entire session. A drug-induced enhancement of performance during the FR-schedule is taken as indication of antianxiety effects. This increased performance is measured by the increased number of electric foot shocks taken during six FR sessions lasting 2 minutes each.

Anticonvulsant effects are observed, for example in the standard Metrazole (pentylenetetrazole) and maximal electroshock tests for assessing anticonvulsant activity, e.g. orally in the rat.

Male Wistar rats (130-175 g) are fasted for 18 hours but allowed water ad libitum prior to testing. The test compound is administered in a cornstarch vehicle by oral intubation in a volume of 10 ml/Kg of body weight. One hour after administration of the test compounds, the animals are administered intravenously (caudal vein) a dose of 24 mg/Kg of Metrazole in water in a volume of 2.5 ml/Kg of body weight. The rats are immediately placed in plexiglas cylinders and observed for clonic seizures of at least 5 seconds duration during the next 60 seconds. The $ED_{50}$ is the dose at which half the animals are protected from Metrazole induced clonic seizures during the observation periods.

Benzodiazepine antagonism is measured by the antagonism of the anticonvulsant activity of diazepam in the rat Metrazole model. Diazepam (5.4 mg/kg/po) and test compound are administered 1 hour before the Metrazole challenge.

In the maximal electroshock procedure for assessing anticonvulsant activity in rats, seizures are induced by applying 150 mA of electric current for 0.2 sec through corneal electrodes two hours after oral administration of test compound as described for the Metrazole test above. The $ED_{50}$ is the dose at which half the animals are protected from electroshock induced seizures during the 5 seconds observation period.

Illustrative of the invention the compounds of examples 2, 5a and 9 exhibit an $IC_{50}$ of about 0.2 nM, 3 nM and 9 nM respectively in the in vitro benzodiazepine receptor assay. Furthermore, e.g. the compound of example 1 inhibits flunitrazepam binding by about 75% in vivo at a dose of 30 mg/kg p.o. in the mouse.

The compounds of the invention also act as adenosine antagonists. Such activity is assessed by determination of inhibition of adenosine activation of adenylate cyclase in vesicular preparations from guinea pig brains, essentially as described in J. Neurochem. 22, 1031 (1974).

Accordingly, the compounds of the invention are useful nervous system active agents, e.g. as benzodiazepine receptor modulators for example in the treatment or management of nervous systems disorders such as anxiety, convulsive conditions (epilepsy) and depression in mamamals. They are also useful intermediates in the preparation of other valuable products, especially of pharmacologically active pharmaceutical compositions.

The compounds of the invention, the compounds of formula IA or IB and salts, derivatives or tautomers thereof, are advantageously prepared by methods known per se, according to the following processes:
(a) reacting a compound of formula VII

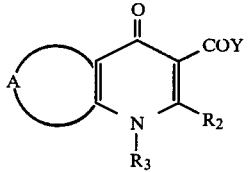

(VII)

wherein A, $R_2$ and $R_3$ have meaning as previously defined and Y is lower alkoxy with a compound of the formula VIII

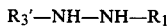 (VIII)

wherein $R_1$ has meaning as previously defined, and $R_3'$ is hydrogen;

(b) reacting a compound of the formula IX

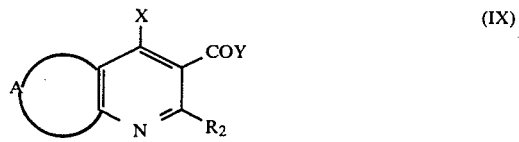

wherein A and $R_2$ have meaning as previously defined; X represents reactive etherified or esterified hydroxy; and Y represents lower alkoxy; with a compound of formula VIII wherein $R_1$ has meaning as previously defined, and $R_3'$ represents hydrogen or lower alkyl;

(c) ring closing a compound of formula IX wherein X is $-NR_3'-NHR_1$ and Y is lower alkoxy or hydroxy; or X is hydroxy, reactive esterified or etherified hydroxy and Y is $-NR_1NHR_3'$; and wherein A, $R_1$, $R_2$ and $R_3'$ have meaning as previously defined; and if desired, converting a resulting compound of formula IA or IB into another compound of the invention; and, if desired, converting a resulting compound of formula IA or IB into a salt thereof or liberating a free compound from such a salt.

The compounds of the invention may also be prepared analogously to other methods known per se, e.g. those disclosed in U.S. Pat. No. 4,312,870.

The condensation according to process (a) is carried out preferably at a temperature range of about 50° to 180°, advantageously in the presence of inert solvents such as aliphatic or aromatic hydrocarbons and ethers such as toluene, xylene, biphenyl and/or diphenyl ether, advantageously e.g. while distilling off the alkanol and water generated, or in the presence of dehydrating agents, such as molecular sieves.

The starting materials of formula VIII are known or may be prepared by methods well-known to the art, e.g. according to e.g. U.S. Pat. No. 3,429,887 and the examples herein.

The starting materials of formula VIII are also known or are prepared by methods well known to the art.

The condensation according to process (b) above is carried out with an excess or equivalent amount of a compound of formula VIII advantageously and depending on the nature of the reactants at temperatures between about 50° and 200° and preferably in an inert solvent e.g. a lower alkanol such as amyl alcohol, n-butyl alcohol or ethanol, an aliphatic or aromatic hydrocarbon such as toluene, xylene or biphenyl, an aromatic ether, such as diphenyl ether or mixtures thereof.

The starting materials of formula IX are known or are prepared by methods well known to the art, e.g. according to U.S. Pat. No. 3,786,043 and the examples herein.

In starting materials of formula IX and IXa below, when X represents reactive esterified hydroxy said group is preferably halogen such as chloro or bromo or, lower alkylsulfonyloxy such as methanesulfonyloxy or when X represents reactive etherified hydroxy said group is preferably lower alkoxy such as methoxy, or aryloxy such as phenoxy.

The ring closure of compounds of formula IX according to process (c) is carried out preferably at a temperature range of about 50° to 200°, advantageously in the presence of inert solvents such as aliphatic or aromatic hydrocarbons, such as toluene, xylene or biphenyl, ethers such as diphenyl ether, alkanols such as n-butanol, with or without a base (such as an alkali metal alkoxide, e.g. sodium ethoxide), a dehydrating agent (such as molecular sieves) or a condensing agent (such as N-ethoxycarbonyl-2-ethoxy-1,2-dihydroquinoline), depending on the nature of X and Y.

Advantageously a condensing agent or dehydrating agent is used for the ring closure of compounds of formula IX wherein Y represents hydroxy.

The starting materials for process (c) of formula IX wherein X is —NR$_3$'—NHR$_1$ and Y is lower alkoxy or hydroxy may be obtained by condensation of a compound of formula IX wherein X represents reactive etherified or esterified hydroxy and Y represents lower alkoxy with a hydrazine of formula VIII, wherein R$_1$ and R$_3$' are as previously defined, in an inert solvent, preferably at a temperature range of about 0° to 75°, and hydrolysis if so required.

The hydrazide starting materials of formula IX wherein X is hydroxy, esterified or etherified hydroxy and Y is —NR$_1$NHR$_3$' are advantageously prepared by condensing a compound of formula IXa

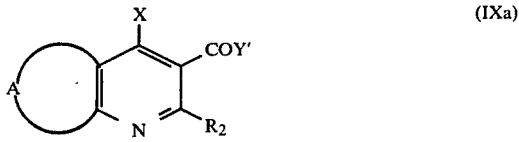

(IXa)

wherein X represents hydroxy, esterified or etherified hydroxy, COY' represents a reactive functionalized carboxy group (such as an acid halide or a mixed anhydride group) and A and R$_2$ are as previously defined, with a hydrazine of formula VIII or with an NHR$_3$'-acylated derivative thereof (such as HNR$_1$—NR$_3$'—COCF$_3$) wherein R$_1$ and R$_3$' are as previously defined, and subsequently deacylating the resulting acyl substituted hydrazide.

A preferred starting material of formula IXa is the appropriately ring-fused and substituted compound of formula IXa wherein X and Y' represent chloro.

The compounds of the invention so obtained can be converted into other compounds of formula IA or IB according to known methods.

For example compounds of formula IA or IB with R$_3$ or R$_3$'=H can be 1-substituted with reactive esters of R$_3$—OH, e.g. such of hydrohalic, aliphatic or aromatic sulfonic acids, such as R$_3$-(halides, sulfates, aliphatic or aromatic sulfonates), e.g. methyl iodide, dimethyl sulfate, methyl mesylate or tosylate, in order to yield the 1-substituted compounds of Formula IB. Those of Formula IA are similarly obtained from the corresponding alkali metal salts, e.g. the sodium salt, whereby 5-substitution occurs. The metal derivative intermediates are obtained by metallation with reactive organometallic agents such as lithium diisopropylamide, with alkali metal alkoxides such as sodium methoxide, or thallous ethoxide, or alkali metal hydrides such as sodium or potassium hydride.

Finally, the compounds of the invention are either obtained in the free form, or as a salt thereof whenever applicable. Any resulting free base can be converted into a corresponding acid addition salt, preferably with the use of a pharmaceutically acceptable acid or anion exchange preparation, or any resulting salt can be converted into the corresponding free base, for example, with the use of a stronger base, such as a metal or ammonium hydroxide or a basic salt, e.g. an alkali metal hydroxide or carbonate, or a cation exchange preparation. Said acid addition salts are preferably such of pharmaceutically acceptable inorganic or organic acids described previously.

Compounds of formula IA or IB with R$_3$ or R$_3$' being hydrogen can also be converted into the corresponding metal salts by e.g. treatment with the alkaline or alkaline earth metal hydroxides or carbonates.

These or other salts, for example, the picrates, can also be used for purification of the bases obtained; the bases are converted into salts, the salts are separated and the bases are liberated from the salts.

In view of the close relationship between the free compounds and the compounds in the form of their salts, whenever a compound is referred to in this context, a corresponding salt is also intended, provided such is possible or appropriate under the circumstances.

The compounds including their salts, can also be obtained in the form of their hydrates or include other solvents used for crystallization.

In case mixtures of isomers of any the above compounds, e.g. of formula I to IX are obtained, these can be separated into the single isomers by methods in themselves known, e.g. by fractional distillation, crystallization and/or chromatography.

The above-mentioned reactions are carried out according to standard methods, in the presence or absence of diluents, preferably such as are inert to the reagents and are solvents thereof, of catalysts, condensing or said other agents respectively and/or inert atmospheres, at low temperatures, room temperature or elevated temperatures, preferably near the boiling point of the solvents used, at atmospheric or superatmospheric pressure.

The invention further includes any variant of the present processes, in which an intermediate product obtainable at any stage thereof is used as starting material and the remaining steps are carried out, or the process is discontinued at any stage thereof, or in which the starting materials are formed under the reaction conditions, or in which the reaction components are used in the form of their salts or pure isomers. Mainly those starting materials should be used in said reactions, that lead to the formation of those compounds, indicated above as being especially valuable.

The pharmacologically active compounds of the invention are useful in the manufacture of pharmaceutical compositions comprising an effective amount thereof in conjunction or admixture with excipients suitable for either enteral or parenteral application. Preferred are tablets and gelatin capsules comprising the active ingredient together with (a) diluents, e.g. lactose, dextrose, sucrose, mannitol, sorbitol, cellulose and/or glycine; (b) lubricants, e.g. silica, talcum, stearic acid, its magnesium or calcium salt and/or polyethyleneglycol; for tablets, also (c) binders, e,g, magnesium aluminum silicate, starch paste, gelatin, tragacanth, methylcellulose, sodium carboxymethylcellulose and/or polyvinylpyrrolidone; if desired, (d) disintegrants, e.g. starches, agar, alginic acid or its sodium salt, or effervescent mixtures; and/or (e) absorbents, colorants, flavors and sweeteners. Injectable compositions are preferably aqueous isotonic solutions or suspensions, and suppositories are advantageously prepared from fatty emulsions or suspensions. Said compositions may be sterilized and/or contain adjuvants, such as preserving, stabilizing, wetting or emulsifying agents, solution promoters, salts for regulating the osmotic pressure and/or buffers. In addition, they may also contain other therapeutically valuable substances. Said compositons are prepared according to conventional mixing, granulating or coating methods, respectively, and contain about 0.1 to 75%, preferably about 1 to 50%, of the active ingredient. A unit dosage for a mammal of about 50 to 70 Kg weight may contain between about 5 and 100 mg of the active ingredient.

The following examples are intended to illustrate the invention and are not to be construed as being limitations thereon. Temperatures herein are given in degrees Centigrade, and all parts whenever given are parts by weight. If not mentioned otherwise, all evaporations are performed under reduced pressure, preferably between about 15 and 100 mm Hg. Proportions whenever given for liquids are in parts by volume.

EXAMPLE 1

A solution of 2.60 g of ethyl 4-chloro-1,6-naphthyridine-3-carboxylate and 1.25 g of phenylhydrazine in 32 ml of methanol is stirred at 22° for 18 hours, then refluxed for 3 hours. The resultant slurry is allowed to cool down to room temperature and filtered, obtaining 2-phenyl-pyrazolo[4,3-c][1,6]-naphthyridin-3(5H)-one hydrochloride, mp 310°; IR (KBr) 750, 756, 777, 802, 843 cm$^{-1}$. This hydrochloride salt is dissolved in 1N sodium hydroxide and filtered. Ammonium chloride (10 g) is added to the filtrate, the resulting precipitate is collected, and is crystallized from methanol to yield the free base, 2-phenyl-pyrazolo[4,3-c][1,6]naphthyridin-3(5H)-one, m.p. 334°–337°.

The starting material is prepared as follows:

A mixture of 9.3 g of ethyl 4-hydroxy-1,6-naphthyridine-3-carboxylate (prepared according to J. Org. Chem. 15, 1224 (1950)) and 56 ml of phosphorous oxychloride is refluxed for 2 hours 40 minutes, then evaporated to dryness and the residue is treated with cold dilute ammonium hydroxide and methylene chloride. Insoluble material is removed by filtration, then organic layer is separated, washed with brine, dried over sodium sulfate and evaporated to dryness to yield ethyl 4-chloro-1,6-naphthyridine-3-carboxylate.

EXAMPLE 2

A solution of 3.8 g of ethyl 4-chloro-1,6-naphthyridine-3-carboxylate and 1.82 g of p-chlorophenylhydrazine in 30 ml of methanol is stirred at 22° for 3 hours, then refluxed for 3 and a half hours. The reaction mixture is then allowed to cool down to room temperature, and filtered collecting 2-p-chlorophenyl-pyrazolo[4,3-c][1,6]naphthyridin-3(5H)-one hydrochloride, m.p. above 345°; IR (KBr) 776, 813, 823, 842, 896 cm$^{-1}$. This hydrochloride salt is converted to the corresponding free base in the same manner as described in Example 1, m.p. above 360°; IR (KBr) 748, 764, 785, 790, 825, 840, 895 cm$^{-1}$.

EXAMPLE 3

To a slurry of 1.5 g of ethyl 4-hydroxy-1,5-naphthyridine-3-carboxylate (prepared according to J. Inorg. Nucl. Chem., (1966) 28, 2439) in 17 ml of dimethylformamide is added 0.907 g of oxalyl chloride in 2 ml of methylene chloride while maintaining the reaction temperature between −25° and −30°. The mixture is stirred at −25° for 35 minutes. A solution of 0.995 g of diisopropylethylamine and 0.833 g of phenylhydrazine in 4 ml of methylene chloride is added to the mixture in 8 minutes at −30° to −25°. The mixture is then stirred for 30 minutes at −25°, 20 minutes at 0° and 40 minutes at 23°. The resultant dark purple solution is poured into 60 ml of water. Dark precipitate is collected, washed with water and crystallized from methanol to yield 2-phenyl-pyrazolo[4,3-c][1,5]naphthyridin-3(5H)-one, m.p. 314°–316°.

EXAMPLE 4

A suspension of ethyl 4-[2-(4-pyridyl)hydrazino]-1,6-naphthyridin-3-carboxylate hydrochloride (1.76 g) in 50 ml of n-butanol is refluxed for 20 hours. The mixture is cooled down to room temperature and filtered. Collected solid is dissolved in aqueous sodium hydroxide and stirred at room temperature for 21 hours, then filtered. The filtrate is acidified with 1N hydrochloric acid to precipitate a solid, which is collected, washed successively with aqueous methanol, methanol and acetone to yield 2-(4-pyridyl)-pyrazolo[4,3-c][1,6]naphthyridin-3(5H)-one hydrochloride, m.p. above 345°; IR (KBr) 726, 746, 791, 833, 898 cm$^{-1}$.

The starting material is prepared as follows:

A solution of 2.36 g of ethyl 4-chloro-1,6-naphthyridine-3-carboxylate and 1.53 g of 4-hydrazinopyridine hydrochloride in 37 ml of methanol is stirred for 19 hours at room temperature, then refluxed for 4 hours. The reaction mixture is then cooled in an ice bath, and solid is collected by filtration, washed successively with methanol and ether to yield ethyl 4-[2-(4-pyridyl)hydrazino]-1,6-naphthyridine-3-carboxylate hydrochloride.

EXAMPLE 5

(a) A solution of 2.84 g of ethyl 4-chloro-1,6-naphthyridine-3-carboxylate and 1.35 g of 3-hydrazinopyridine in 36 ml of methanol is stirred at room temperature for 2.5 hours, then refluxed for 4.5 hours, then cooled in an ice bath and filtered. Collected solid is washed with methanol, then with ether to yield 2-(3-pyridyl)-pyrazolo[4,3-c][1,6]naphthyridin-3-(5H)-one hydrochloride, m.p. 302°–305°.

(b) In an analogous manner, from 2.6 g of ethyl 4-chloro-1,6-naphthyridine-3-carboxylate and 1.34 g of 2-hydrazino-thiazole (prepared according to Can. J. Chem. 1970, 48, 3554), there is obtained 2-(2-thiazolyl)-pyrazolo[4,3-c][1,6]naphthyridin-3(5H)-one hydrochloride, m.p. above 345°; IR (KBr) 730, 746, 786, 811, 854 cm$^{-1}$.

EXAMPLE 6

A solution of 1.75 g of ethyl 4-chloro-1,6-naphthyridine-3-carboxylate and 1.17 g of 2-hydrazinopyrimidine hydrochloride (prepared according to Yakugakuzasshi, 1953, 73, 598) in 60 ml of n-butanol is refluxed for 3 hours. The resultant slurry is cooled to room temperature and filtered. Collected solid is washed with ethanol, then with ether to yield 2-(2-pyrimidyl)-pyrazolo[4,3-c][1,6]naphthyridin-3(5H)-one hydrochloride, m.p. above 350°; IR (KBr) 782, 791, 820, 830, 871 cm$^{-1}$.

EXAMPLE 7

A mixture of 3.0 g of ethyl 4-chloro-7-methyl-1,8-naphthyridine-3-carboxylate (prepared according to U.S. Pat. No. 3,786,043) and 1.42 g of phenylhydrazine in 30 ml of n-butanol is refluxed for 18 hours. The mixture is chilled in an ice bath and filtered to give a solid which is taken up in 50 ml of 1N sodium hydroxide and sufficient water to dissolve. The resulting solution is filtered to remove insoluble, washed with ether and neutralized with 3.0 g of ammonium chloride. The resulting mixture is filtered collecting a solid which is washed with water and dried to yield 7-methyl-2-phenylpyrazolo[4,3-c][1,8]naphthyridin-3(5H)-one hemihydrate, m.p. 305°–308°.

EXAMPLE 8

A mixture of 2.25 g of ethyl 4-chloro-6,8-dimethoxy-1,2-naphthyridine-3-carboxylate and 1.2 g of p-chlorophenylhydrazine in 180 ml of xylene is heated at reflux overnight, then cooled and extracted with 1N sodium hydroxide (300 ml). The aqueous alkali phase is separated, washed with ether and neutralized with 20 g of ammonium chloride to precipitate a solid. The solid is collected and washed with ethanol to yield 2-(4-chlorophenyl)-6,8-dimethoxy-pyrazolo[4,3-c][1,7]naphthyridin-3(5H)-one, m.p. 318°–321°.

The starting material is prepared as follows:

A mixture of 5.6 g of 3-amino-2,6-dimethoxypyridine and 8.8 g of diethyl ethoxymethylenemalonate is stirred at room temperature overnight to form a solid. The solid is collected, dissolved in ethyl acetate, treated with decolorizing charcoal and evaporated to dryness to yield diethyl N-[3-(2,6-dimethoxypyridyl)]-aminomethylenemalonate, m.p. 78°–81°.

Diethyl N-[3-(2,6-dimethoxypyridyl)]-aminomethylenemalonate (12.5 g) in 250 ml of an eutectic mixture of diphenyl ether and biphenyl (Dowtherm ®) is heated at reflux for 5 hours under nitrogen atmosphere, then cooled to room temperature to deposit a solid. The solid is collected and washed with ether to yield ethyl 4-hydroxy-6,8-dimethoxy-1,7-naphthyridine-3-carboxylate, m.p. 311° (dec.).

A solution of 3.5 g of oxalyl chloride in 5 ml of dry acetonitrile is added dropwise to anhydrous dimethylformamide at −30°. After 20 minutes, 7.0 g of ethyl 4-hydroxy-6,8-dimethoxy-1,7-naphthyridine-3-carboxylate is added at −30°. Reaction temperature is kept between −20° and −30° for 30 minutes, then allowed to warm up to room temperature and evaporated to dryness. Residue is taken up in chloroform, washed with cold sodium bicarbonate aqueous solution, dried over magnesium sulfate, treated with decolorizing charcoal and evaporated to dryness to yield ethyl 4-chloro-6,8-dimethoxy-1,7-naphthyridine-3-carboxylate, m.p. 200°–210°.

EXAMPLE 9

A mixture of 3.2 g of ethyl 4-chlorol-thieno[2,3-b]pyridine-3-carboxylate (prepared according to J. Heterocyclic Chem., 1977, 14, 807) and 2.08 g of 4-chlorophenylhydrazine in 50 ml of n-butanol is refluxed for 48 hours. The reaction mixture is cooled in an ice bath and the resulting precipitate is collected, washed with a small amount of n-butanol to yield a solid. The solid is treated with ether and 1N sodium hydroxide (20 ml) and water (50 ml). The aqueous phase is washed with ether, then neutralized with ammonium chloride (2 g) to precipitate a yellow solid. The solid is collected, washed with water and dried to yield 2-(4-chlorophenyl)-thieno[2,3-b]pyrazolo[3,4-d]pyridin-3(5H)-one hydrate, m.p. 310°–313°.

EXAMPLE 10

Compounds which are prepared analogous to the methods illustrated by the previous examples:

Example

10/a: 2-(4-Chlorophenyl)-7-methyl-pyrazolo[4,3-c][1,8]-naphthyridin-3(5H)-one 2/3 hydrate, m.p. 340°–342°.

10/b: 7-Methyl-2-(3-pyridyl)-pyrazolo[4,3-c][1,8]naphthyridin-3(5H)-one hydrate, m.p. 314°–317°.

10/c: 7-Methyl-2-(2-pyrimidyl)-pyrazolo[4,3-c][1,8]naphthyridin-3(5H)-one hydrochloride hemihydrate, m.p. 310°–315°.

10/d: 6,8-Dimethoxy-2-phenyl-pyrazolo[4,3-c][1,7]-naphthyridin-3(5H)-one, m.p. 303°–306°.

EXAMPLE 11

Compounds of formulae I, II, III, IV, V and VI which can be prepared analogous to the methods illustrated by the previous examples:

| Example | Formula | R$^1$ | Other Substituents |
|---|---|---|---|
| 11/a | II | 4-pyrimidyl | 7-methyl |
| 11/b | III | 6-Me—3-pyridyl | — |
| 11/c | III | 2-quinolyl | 8-methyl |
| 11/d | IV | 5-MeO—2-pyrimidyl | 7-methyl |
| 11/e | V | 5-chloro-2-thiazolyl | 7-chloro |
| 11/f | VI | 5-chloro-2-pyridyl | 4,6-dimethyl |
| 11/g | VI | 5-pyrimidyl | 4,6,7-trimethyl |
| 11/h | VI | 4-chlorophenyl | — |

Starting Materials

Example

11/a: 4-Hydrazinopyrimidine, J. Chem. Soc., 1955, 3478.

11/b: Ethyl 4-chloro-1,7-naphthyridine-3-carboxylate from ethyl 4-hydroxy-1,7-naphthyridin-3-carboxylate 7-oxide of J. Org. Chem., 19, 2008 (1954)

11/c: Ethyl 4-chloro-6-methyl-1,7-naphthyridine-3-carboxylate from ethyl 4-hydroxy-6-methyl-1,7-naphthyridine-3-carboxylate of U.S. Pat. No. 3,429,887.

11/d: 5-Methoxy-2-hydrazinopyrimidine from 2-chloro-5-methoxypyrimidine, of J. Chem. Soc., 1960, 4590. Ethyl 4-chloro-2-methyl-thieno[2,3-b]pyridine-5-carboxylate from ethyl 4-hydroxy-2-methyl-thieno[2,3-b]pyridine-5-carboxylate of U.S. Pat. No. 3,997,545.

11/e: Ethyl 2,7-dichloro-thieno[3,2-b]pyridine-6-carboxylate of European patent application No. 46,990.

11/f: Ethyl 7-chloro-3,5-dimethyl-imidazo[4,5-b]pyridine-6-carboxylate of J. heterocyclic Chem., 14, 813 (1977).

11/g: Ethyl 7-chloro-2,3,5-trimethyl-imidazo[4,5-b]pyridine-6-carboxylate of J. Heterocyclic Chem., 14, 813 (1977).

EXAMPLE 12

Preparation Of 10,000 tablets each containing 10 mg of the active ingredient:

| | |
|---|---|
| 2-(3-pyridyl)-pyrazolo[4,3-c][1,6] naphthyridin-3(5H)—one hydrochloride | 100.00 g |
| Lactose | 1,157.00 g |
| Corn Starch | 75.00 g |
| Polyethylene glycol 6,000 | 75.00 g |
| Talcum powder | 75.00 g |
| Magnesium stearate | 18.00 g |
| Purified water | q.s. |

Procedure

All the powders are passed through a screen with openings of 0.6 mm. Then the drug substance, lactose, talcum, magnesium stearate and half of the starch are mixed in a suitable mixer. The other half of the starch is suspended in 40 ml of water and the suspension added to the boiling solution of the polyethylene glycol in 150 ml of water. The paste formed is added to the powders which are granulated, if necessary, with an additional amount of water. The granulate is dried overnight at 35°, broken on a screen with 1.2 mm openings and compressed into tablets using concave punches with 6.4 mm diameter, uppers bisected.

EXAMPLE 13

Preparation of 10,000 capsules each containing 25 mg of the active ingredient:

Formula

| | |
|---|---|
| 2-(4-chlorophenyl)-thieno[2,3-b]pyrazolo-[3,4-d]pyridin-3(5H)—one | 250.0 g |
| Lactose | 1,650.0 g |
| Talcum powder | 100.0 g |

Procedure

All the powders are passed through a screen with openings of 0.6 mm. Then the drug substance is placed in a suitable mixer and mixed first with the talcum, then with the lactose until homogenous. No. 3 capsules are filled with 200 mg each, using a capsule filling machine.

Analogously tablets or capsules are prepared from the remaining compounds of the invention, e.g. those illustrated by the examples herein.

What is claimed is:

1. A compound of the formula

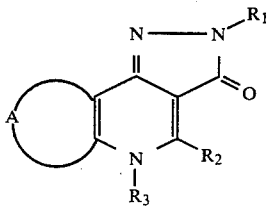

(IA)

or

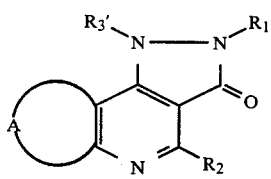

(IB)

wherein A together with the two carbon atoms to which it is attached represents a fused heterocyclic ring selected from (a) thieno, furo, and N-unsubstituted or N-lower alkyl substituted pyrrolo, wherein the carbon atoms in any of said rings are unsubstituted or one of them is substituted by lower alkyl, carbo-(lower)-alkoxy, halogen or trifluoromethyl; (b) N-unsubstituted or lower alkyl substituted-imidazo, wherein the carbon atom in said ring is unsubstituted or substituted by lower alkyl, lower alkoxy, halogen or trifluoromethyl; (c) thiazolo, oxazolo, isoxazolo, and pyridazino, wherein the carbon atoms forming any of said rings are unsubstituted or one or two are substituted by lower alkyl, lower alkoxy or halogen; (d) pyrimido and pyrazino wherein the carbon atoms in any of said rings are unsubstituted or one is substituted by lower alkyl or lower alkoxy; $R_1$ represents phenyl, or phenyl mono- or disubstituted by lower alkyl, lower alkoxy, halogen or trifluoromethyl; or $R_1$ represents an aromatic heterocyclic radical selected from pyridyl, quinolyl, isoquinolyl, pyrimidyl and thiazolyl, or any said heterocyclic radical mono- or di-substituted by lower alkyl, lower alkoxy or halogen; $R_2$, $R_3$ and $R_3'$ independently represent hydrogen or lower alkyl; or a pharmaceutically acceptable salt thereof.

2. A compound according to claim 1 of formula IA or IB wherein A together with the two carbon atoms to which it is attached represent fused 2,3- or 3,2-thieno, and the carbon atoms in said thieno ring are unsubstituted or monosubstituted by lower alkyl, carbo-(lower)-alkoxy, halogen or trifluoromethyl; $R_1$, $R_2$, $R_3$ and $R_3'$ have meaning as given in claim 1; or a pharmaceutically acceptable salt thereof.

3. A compound according to claim 2 of formula IV

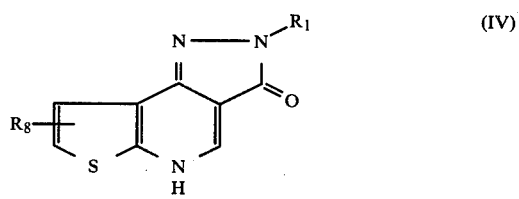

(IV)

wherein $R_1$ represents phenyl or phenyl mono- or disubstituted by lower alkyl, lower alkoxy, halogen or trifluoromethyl; or an aromatic heterocyclic radical selected from pyridyl, quinolyl, isoquinolyl, pyrimidyl and thiazolyl, or any said heterocyclic radical mono- or disubstituted by lower alkyl, lower alkoxy or halogen; $R_8$ represents hydrogen, lower alkyl, carbo-(lower)-alkoxy, halogen or trifluoromethyl; or a tautomer thereof; or a pharmaceutically acceptable salt thereof.

4. A compound according to claim 2 of formula V

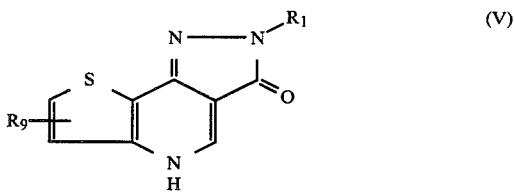

(V)

wherein $R_1$ represents phenyl or phenyl mono- or disubstituted by lower alkyl, lower alkoxy, halogen or trifluoromethyl; or an aromatic heterocyclic radical selected from pyridyl, quinolyl, isoquinolyl, pyrimidyl and thiazolyl, or any said heterocyclic radical mono- or disubstituted by lower alkyl, lower alkoxy or halogen; $R_9$ represents hydrogen, lower alkyl, carbo-(lower)-alkoxy, halogen or trifluoromethyl; or a tautomer thereof; or a pharmaceutically acceptable salt thereof.

5. A compound according to claim 1 of formula IA or IB wherein A together with the two carbon atoms to which it is attached represents fused N-unsubstituted or N-lower alkyl substituted 5,4-imidazo, and the carbon atom in said 5,4-imidazo ring is unsubstituted or substituted by lower alkyl, phenyl or phenyl mono-substituted by lower alkyl, lower alkoxy, halogen, or trifluoromethyl; $R_1$, $R_2$, $R_3$ and $R_3'$ have meaning as given claim 1; or a pharmaceutically acceptable salt thereof.

6. A compound according to claim 5 of formula VI

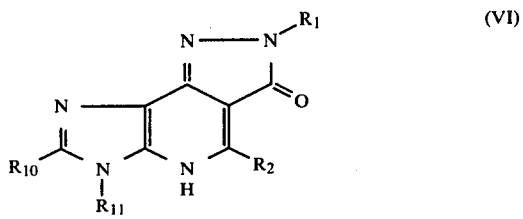

(VI)

wherein $R_1$ represents phenyl or phenyl mono- or disubstituted by lower alkyl, lower alkoxy, halogen or trifluoromethyl; or an aromatic heterocyclic radical selected from pyridyl, quinolyl, isoquinolyl, pyrimidyl and thiazolyl, or any said heterocyclic radical substituted by lower alkyl, lower alkoxy or halogen; $R_2$ represents hydrogen or lower alkyl; $R_{10}$ represents hydrogen, lower alkyl, phenyl or phenyl monosubstituted by lower alkyl, lower alkoxy, halogen or trifluoromethyl; $R_{11}$ represents hydrogen or lower alkyl; or a tautomer thereof; or a pharmaceutically acceptable salt thereof.

7. A compound of claim 3 being 2-p-chlorophenyl-thieno[2,3-b]pyrazolo[4,3-d]pyridin-3(5H)-one or a pharmaceutically acceptable salt thereof.

8. A compound of claim 4 being 2-(3-pyridyl)-thieno[3,2-b]pyrazolo-[4,3-d]pyridin-3(5H)-one or a pharmaceutically acceptable salt thereof.

9. An anxiolytic pharmaceutical composition suitable for oral or parenteral administration to mammals comprising an effective anxiolytically amount of a compound of claim 1 having anxiolytic activity in combination with one or more pharmaceutically acceptable carriers.

10. A method for treating anxiety in mammals which comprises administering to a mammal in need thereof an effective amount of a composition of claim 9.

11. A process for preparing a compound of claim 1 comprising (a) reacting a compound of formula VII

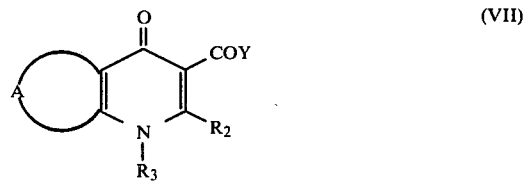

(VII)

wherein A, $R_2$ and $R_3$ have meaning as defined in claim 1, and Y is lower alkoxy; with a compound of the formula VIII

$R_3'$—NH—NH—$R_1$ (VIII)

wherein $R_1$ has meaning as defined in claim 1, and $R_3'$ is hydrogen;

(b) reacting a compound of the formula IX

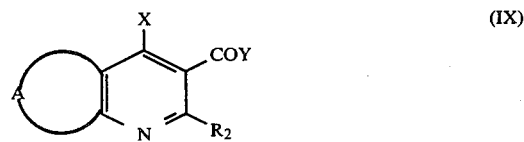

(IX)

wherein A and $R_2$ have meaning as defined in claim 1; X represents reactive etherified or esterified hydroxy; and Y represents lower alkoxy; with a compound of formula VIII wherein $R_1$ has meaning as defined in claim 1; and $R_3'$ represents hydrogen or lower alkyl;

(c) ring closing a compound of formula IX wherein X is —$NR_3'$—$NHR_1$ and Y is lower alkoxy or hydroxy; or X is hydroxy, reactive esterified or etherified hydroxy and Y is —$NR_1NHR_3'$; and wherein A, $R_1$, $R_2$ and $R_3'$ have meaning as defined in claim 1; and if desired, converting a resulting compound of formula IA or IB into another compound of the invention; and, if desired, converting a resulting compound of formula IA or IB into a salt thereof or liberating a free compound from such a salt.

* * * * *